United States Patent

Wu

[11] 4,334,965
[45] Jun. 15, 1982

[54] PROCESS FOR RECOVERY OF OLEFINIC NITRILES

[75] Inventor: Hsin-Chih Wu, Parma, Ohio

[73] Assignee: Standard Oil Company, Cleveland, Ohio

[21] Appl. No.: 221,666

[22] Filed: Dec. 31, 1980

[51] Int. Cl.³ .................. B01D 3/40; C07C 121/32
[52] U.S. Cl. .................................. 203/25; 203/14;
    203/42; 203/84; 203/85; 203/DIG. 3;
    203/DIG. 19; 159/17 P; 260/465.9
[58] Field of Search .............. 203/85, 76, 84, 79,
    203/83, DIG. 19, 99, 42, DIG. 3, 25, 14, 92, 93,
    95–97; 202/174, 187, 192, 182–184; 260/465.9,
    465.3; 55/68, 84; 208/311; 159/17 R, 17 P

[56] References Cited

U.S. PATENT DOCUMENTS

| | | | |
|---|---|---|---|
| 2,053,111 | 9/1936 | Reich | 202/174 |
| 2,126,974 | 8/1938 | Reich | 202/174 |
| 2,510,548 | 6/1950 | Brunjes | 202/174 |
| 3,636,067 | 1/1972 | Lovett et al. | 260/465.9 |
| 3,734,943 | 5/1973 | Fitzgibbons et al. | 260/465.9 |
| 3,895,050 | 7/1975 | Sheely | 260/465.9 |
| 3,936,360 | 2/1976 | Wu | 260/465.9 |
| 4,059,492 | 11/1977 | Hausweiker et al. | 260/465.9 |
| 4,141,826 | 2/1979 | Alford et al. | 260/465.9 |
| 4,166,008 | 8/1979 | Wu et al. | 203/85 |

Primary Examiner—Wilbur L. Bascomb, Jr.
Attorney, Agent, or Firm—John E. Miller, Jr.; Herbert D. Knudsen; Larry W. Evans

[57] ABSTRACT

A multi-stage evaporator is used to remove water from the extracted distillation or stripper tower bottoms recycled as quench liquid to the quench tower of an acrylonitrile purification and recovery system. This results in a significant decrease in the amount of waste quench tower bottoms produced by the system. Use of a multi-effect evaporator represents a significant energy savings as compared with other techniques for decreasing the water content of the recycle stream.

11 Claims, 1 Drawing Figure

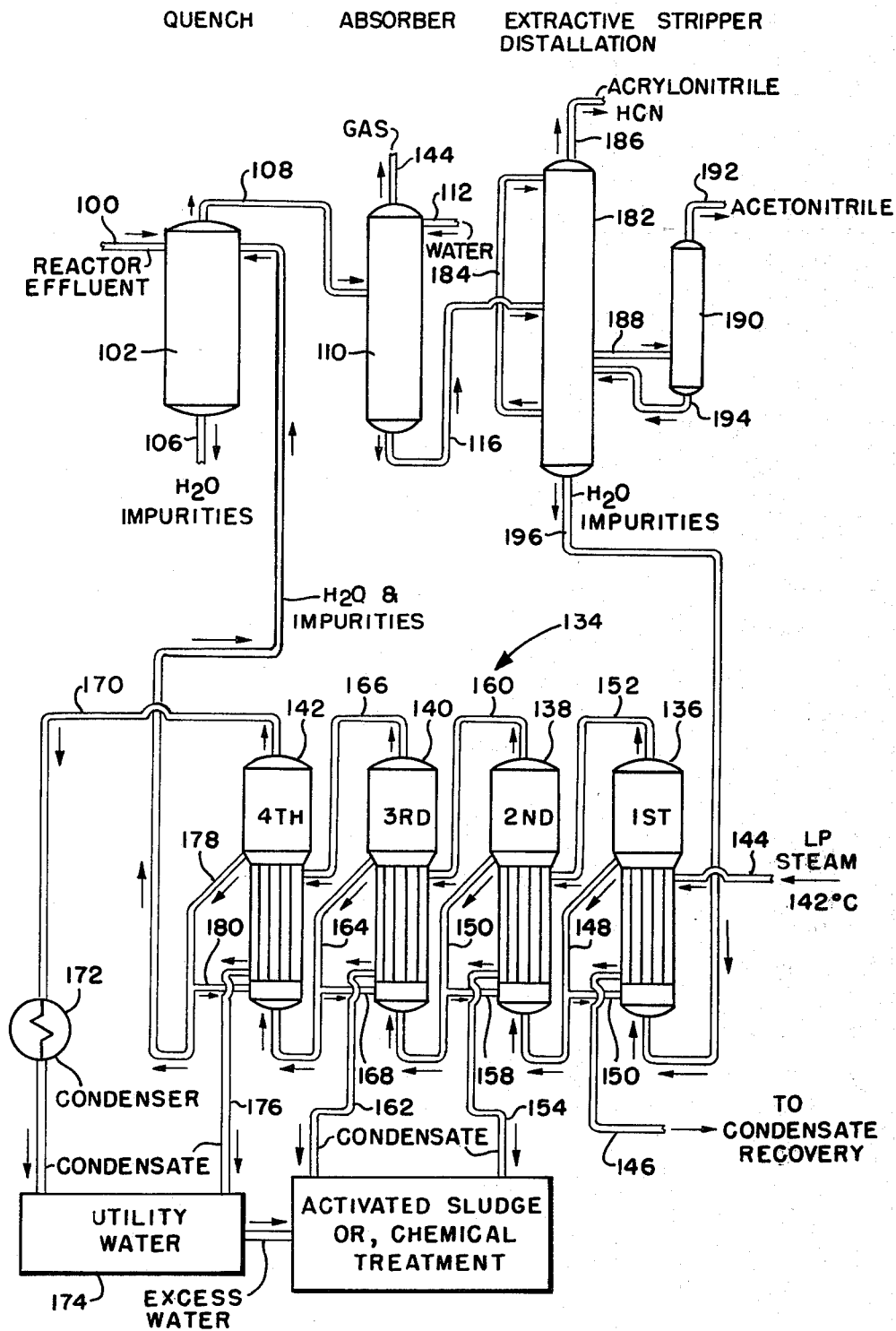

PROCESS FOR RECOVERY OF OLEFINIC NITRILES

BACKGROUND OF THE INVENTION

The present invention is an improvement over the invention described in commonly assigned U.S. Pat. No. 4,166,008, the disclosure of which is incorporated herein by reference.

U.S. Pat. No. 4,166,008 describes an improvement in the known system for recovery and purification of acrylonitrile and methacrylonitrile produced by the ammoxidation of propylene or isobutylene. In accordance with this improvement, a vaporous sidestream is removed from the lower fourth of the column whose bottoms product is used as the quench liquid (extractive distillation column or stripper) for quenching the ammoxidation reactor effluent. By withdrawing this sidestream, it was found that the concentration of heavy organics in the quench bottom streams could be significantly increased while at the same time the total mass flow of this stream significantly decreased. Since the quench tower bottoms are normally disposed of by incineration, this drastic decrease in the amount of quench tower bottoms represented a significant energy savings.

Unfortunately, a penalty associated with this approach is that additional heat must be supplied to the column from which the side stream is taken to account for the associated heat loss. For example, as taught in column 4 of U.S. Pat. No. 4,166,008, a 12% increase in heat input was necessary in the specific embodiment described.

Normally, heat is supplied to the extractive distillation column and stripper column by reboilers using low pressure steam as the heat source. With higher and higher energy costs, it is always desirable to reduce the usage of low pressure steam as much as possible so that excess low pressure steam can be used for other beneficial purposes.

Accordingly, it is an object of the present invention to provide a new system for accomplishing the same results achieved in U.S. Pat. No. 4,166,008, i.e. significant reduction in the amount of quench tower bottoms produced by a technique which requires significantly less energy than the technique described in that patent.

SUMMARY OF THE INVENTION

This and other objects are accomplished by the present invention in accordance with which a multi-effect evaporator is employed to process the raw distillation tower bottoms or stripper bottoms recycled for use as the quench liquid in the quench column. By means of a multi-effect evaporator, 50% or more of the liquid in the recycled stream can be removed therefrom leaving a concentrated recycle stream to serve as the quench liquid in the same way as shown in U.S. Pat. No. 4,166,008. Because multi-effect evaporators are so energy efficient, however, the overall energy costs of this technique are much lower than the technique described in that patent.

Thus, the present invention provides a improvement in the known technique for the recovery of acrylonitrile or methacrylonitrile from an ammoxidation reactor effluent containing acrylonitrile or methacrylonitrile, acetonitrile and heavy organic impurities in which the reactor effluent is cooled by contact with an aqueous quench liquid to produce a gaseous quench effluent containing acrylonitrile or methacrylonitrile, and acetonitrile and a liquid quench bottoms, the quench liquid being obtained by contacting the gaseous quench effluent with water comprising removing water from said quench liquid by multiple effect evaporation prior to contacting said quench liquid with said reactor effluent.

BRIEF DESCRIPTION OF THE DRAWINGS

FIG. 1 is a scematic representation of one embodiment of the invention as applied to the recovery and purification of acrylonitrile; and FIG. 2 is a scematic representation similar to FIG. 1 showing the application of the invention to another purification and recovery system for recovering acrylonitrile.

DETAILED DESCRIPTION

FIG. 1 is a schematic representation of the present invention as applied to the recovery and purification of acrylonitrile.

Referring to the figure, the reactor effluent gas in conduit 100 containing acrylonitrile, HCN, acetonitrile, water vapor and impurities is first passed to a quench column 102. The gas is contacted with quench liquid 130 in the quench column. A bottoms stream containing water and impurities is removed through conduit 106 and sent to waste treatment.

The cooled reactor effluent gases leave the quench system through line 108 and pass as feed to the absorber 110. Wash water enters the absorber at the top through line 112. Non-condensible gases are removed from the absorber through line 114. An aqueous solution containing water, acrylonitrile, acetonitrile and impurities are removed as a bottoms stream through line 116 and passed to the extractive distillation column 118.

Solvent water is introduced to the top of column 118 through line 120 to perform extractive distillation. Acrylonitrile and HCN are removed as an overhead vapor through line 122 and sent to further purification (not shown). A bottoms stream containing acetonitrile and water is removed through line 124 and passed to stripper 126. Heat is added to the stripper to remove acetonitrile as an overhead vapor through line 128. The bottoms stream containing water, heavy organics and other impurities are removed through line 132 and sent back to the quench system. A liquid stream may be removed from the lower half of the stripper through line 120 and used as solvent water to the extractive distillation column.

In accordance with the invention, stripper column bottoms in line 132 are subjected to multi-stage evaporation in a multi-stage evaporator unit generally indicated at 134 prior to being returned via line 130 to quench tower 102 as the quench liquid.

Multiple effective evaporator 134 is composed of four shell and tube heat exchangers 136, 138, 140 and 142 arranged in series. In each heat exchanger, liquid in the tube side of the exchanger is partially evaporated producing a vaporous effluent and a liquid effluent. The liquid effluent is fed to the tube side of the next heat exchanger in the series while the vaporous effluent is fed to the shell side of the same heat exchanger causing additional partial evaporation of the liquid. This technique is continued for as many stages as is necessary to remove the desired amount of water from the stripper bottoms, which are then sent to the quench column for use as the quench liquid. In each stage, condensate produced when the heat-supplying vapor is condensed through heat exchange is recovered and either recycled for reuse or subjected to chemical or biological purification. The details of this procedure are described below.

Stripper column bottoms in line 132 are passed into the tube side of first heat exchanger 136 while low pressure steam is passed through the shell side of this heat exchanger. Heat exchange therein causes the lower pressure steam to condense and the stripper bottoms to partially evaporate. Condensate is removed from first heat exchanger 136 for reuse via line 146.

Heating of the stripper column bottoms in first heat exchanger 136 causes partial separation thereof into vapor and liquid phases. The liquid phase is withdrawn via line 148 and transferred to the tube side of second heat exchanger 138, a portion of the withdrawn liquid being recycled via line 150 to the bottom of the tube side of first heat exchanger 136. Vapor produced in first heat exchanger 136 is withdrawn and transferred via line 152 to the shell side of second heat exchanger 138. Heat exchange in heat exchanger 138 causes condensation of the vapor on the shell side and partial evaporation of the liquid in the tube side, thereby producing liquid in vapor phases in second heat exchanger 138. Condensate produced on the shell side of second heat exchanger 138 is discharged to waste via line 154. This condensate has a relatively low concentration of heavy organics such as polymer and the like and hence can be rendered environmentally acceptable by conventional biological or chemical treatments.

The liquid phase remaining in the tube side of second heat exchanger 138 is transferred via line 156 to the tube side of third heat exchanger 140, a portion of the liquid being recycled via line 158 to the tube side of second heat exchanger 138. Vapor produced in the tube side of second heat exchanger 138 is transferred via line 160 to the shell side of third heat exchanger 140. Again, heat exchange in third heat exchanger 140 causes condensation of the vapor on the shell side to form a condensate which is withdrawn via line 162 and disposed of in the same way as the condensate from second heat exchanger 138.

The liquid and vapor phases produced in the tube side of third heat exchanger 140 are transferred via lines 164 and 166 to the tube and shell sides of fourth heat exchanger 142 with a portion of the liquid phase again being recycled via line 168. The vapor produced in the tube side of fourth heat exchanger 142 is withdrawn via line 170, condensed in condenser 172 and recovered in utility water vessel 174. The condensate from the shell side of heat exchanger 142 is also transferred to utility water vessel 174 via line 176. Both these condensates are of such high purity that it can be used as conventional clean water such as, for example, in the flushing of various process equipment. Liquid recovered from the tube side of fourth heat exchanger 142 is withdrawn via line 178 and after a portion thereof is recycled via line 180 to the tube side of the fourth heat exchanger is transferred via line 130 to quench column 102 as the quench liquid.

By the above means, a significant amount, for example, one-half or more of the water in stripper bottoms 132 can be removed thereby providing a concentrated stripper bottoms much more concentrated in impurities but having a much lower mass flow rate in line 130 for use as quench liquid. This in turn means that the quench tower bottoms recovered in line 106 will likewise have a much higher concentration of impurities but a much lower mass flow rate. Because of the high energy efficiency of the multi-effect evaporator system, however, the energy requirements to operate this system are much less than the system described in U.S. Pat. No. 4,166,008.

A second embodiment of the invention is shown in FIG. 2. The aqueous solution from the absorber 110 is passed through line 116 to a modified extractive distillation column 182. Solvent water is introduced to the top of this column through line 184 to absorb the acetonitrile. Acrylonitrile and HCN are removed overhead as a vapor through line 186. A liquid stream containing acetonitrile and water is removed from the bottom half of this column through line 188 and sent to a small stripping column 190. Acetonitrile passes overhead as a vapor through line 192. A liquid stream containing mostly water is removed from the bottom of column 190 through line 194 and returned to the extractive distillation column. In accordance with the invention, the liquid bottom's stream in line 196 passing out of extractive distillation column 182 is subjected to multiple effect evaporation prior to return to quench column 102.

COMPARATIVE EXAMPLE A AND EXAMPLE 1

An acrylontrile recovery process is performed substantially as shown in the figure. In the Comparative Example A, all of the liquid bottoms stream from the stripper is recycled to the quench column as quench liquid. Example 1 is identical to Comparative Example A except that the stripper column bottoms is processed in accordance with the system shown in the figure by a four-stage multi-effect evaporator operated so as to remove one-half of the water in stripper bottoms.

The tables below show the weight percent polymer and the COD contained in the various process streams of both examples.

TABLE I

| | Weight Percent Polymers | | | | | |
|---|---|---|---|---|---|---|
| Ex. | Strip. Column Btms. | Quench Tower Btms. | 1st Stage Btms. | 2nd Stage Btms. | 3rd Stage Btms. | 4th Stage Btms. |
| Comp A | 1.5 | 10 | — | — | — | — |
| 1 | 1.5 | 25 | 1.62 | 1.81 | 2.18 | 3.00 |

TABLE II

| | Weight Percent COD | | | |
|---|---|---|---|---|
| Ex. | 2nd Stage Conden. | 3rd Stage Conden. | 4th Stage Conden. | Condenser Condensate |
| Comp A | — | — | — | — |
| 1 | 0.20 | 0.11 | 0.05 | 0.04 |

As can be seen in these tables, the condensates produced in the second and third heat exchangers contain extremely small amounts of heavy organics. Thus, they can be directly processed by conventional biological or chemical treatment to produce environmentally acceptable water. Furthermore, the condensate produced in the fourth heat exchanger as well as the condensate produced by the condenser are pure enough to be used for various process purposes such as wash water without further treatment. The condensate produced by the first heat exchanger, since it does not contact any other process stream, is of course highly pure. In addition, because of the removal of water from the stripper bottoms the amount of quench liquid returned to the quench tower is approximately 50% of the stripper bottoms. This means that the amount of quench tower bottoms produced is approximately 40% of the quench tower bottoms produced in the comparative example. Finally, because a four-stage multi-effect evaporator is so energy efficient, the amount of low pressure steam needed to carry out the present invention is only one-third to one-fourth the amount needed to operate this system. Thus, it can be seen that the present invention accomplishes the same advantageous result as U.S. Pat. No. 4,166,008 using significantly less energy.

Although only a single embodiment of the invention has been described above, many modifications can be made without departing from the spirit and scope of the invention. For example, any number of stages can be employed in the multiple effect evaporator. Thus, three stages are beneficial although four are preferred from the standpoint of energy savings. Furthermore, although low pressure steam is shown in the above description as supplying the heat necessary for all the evaporations, any heat source can be employed. In a typical acrylonitrile purifications and recovery plant, however, low pressure steam, that is saturated steam having a pressure of up to 100 psig, normally about 20 to 60 psig, is readily available and is preferably used. Also, the amount of water in the stripper column removed by the multiple effect evaporator can be varied depending primarily upon economics. Finally, it should also be appreciated that the multiple effect evaporator of this invention need not be restricted to use on stripper column bottoms as shown in the above description, but can be employed to concentrate any other process stream which is recycled for use as the quench liquid. For example, a multi-effect evaporator can be used to process the extractive distillation tower bottoms recycled in line 156 of FIG. 2 of U.S. Pat. No. 4,166,008. All such modifications are intended to be included within the scope of the present invention, which is to be limited only by the following claims:

I claim:

1. In a process for the recovery and purification of acrylonitrile or methacrylonitrile from an ammoxidation reactor effluent containing acrylonitrile or methacrylonitrile, acetonitrile and heavy organic impurities which comprises:
   (a) contacting said reactor effluent with an aqueous quench liquid to produce a gaseous quench effluent and a liquid quench bottoms product,
   (b) absorbing said gaseous quench effluent with water to produce a first aqueous solution containing acrylonitrile or methacrylonitrile, acetonitrile and said impurities,
   (c) extractively distilling said first aqueous solution with a water-containing stream to produce a gaseous effluent containing acrylonitrile or methacrylonitrile and a liquid bottoms product containing water, acetonitrile and said heavy organics,
   (d) stripping acetonitrile from said liquid bottoms product thereby producing a stripper bottoms product containing water and said heavy organic impurities, and
   (e) recycling said stripper bottoms product to step (a) to serve as said quench liquid,
the improvement comprising removing water from said stripper bottoms product by multi-effect evaporation prior to returning said stripper bottoms to step (a).

2. The process of claim 1 wherein said reactor effluent contains acrylonitrile.

3. The process of claim 2 wherein water is removed from said stripper bottoms in a plurality of stages, said liquid stripper bottoms being partially evaporated in a first of said stages to produce a first vaporous product and a first liquid residue, said first vaporous product and first liquid residue being subjected to indirect heat exchange in a second of said stages whereby said first vaporous product condenses to form a first condensate and said first liquid product partially evaporates to form a second vaporous product and a second liquid residue.

4. The process of claim 3 wherein water is removed from said stripper bottoms in a multi-effect evaporator having at least three stages.

5. The process of claim 4 wherein said multi-effect evaporator has at least four stages.

6. In a process for the recovery and purification of acrylonitrile or methacrylonitrile from an ammoxidation reactor effluent containing acrylonitrile or methacrylonitrile, acetonitrile and heavy organic impurities which comprises:
   (a) contacting said reactor effluent with an aqueous quench liquid to produce a gaseous quench effluent and a liquid quench bottoms product,
   (b) absorbing said gaseous quench effluent with water to produce a first aqueous solution containing acrylonitrile or methacrylonitrile, acetonitrile and said impurities,
   (c) extractively distilling said first aqueous solution with a water-containing stream to produce a gaseous effluent containing acrylonitrile and a liquid bottoms product containing water and said heavy organics,
   (d) removing a sidestream from the distillation zone of step (c) to recover acetonitrile, and
   (e) recycling at least a part of said liquid bottoms product to step (a) to serve as said aqueous quench liquid,
the improvement comprising removing water from said liquid bottoms product by multi-effect evaporation prior to returning said liquid bottoms product to step (a).

7. The process of claim 6 wherein said reactor effluent contains acrylonitrile.

8. The process of claim 7 wherein water is removed from said liquid bottoms product in a plurality of stages, said liquid bottoms product being partially evaporated in a first of said stages to produce a first vaporous product and a first liquid residue, said first vaporous product and first liquid residue being subjected to indirect heat exchange in a second of said stages whereby said first vaporous product condenses to form a first condensate and said first liquid product partially evaporates to form a second vaporous product and a second liquid product.

9. The process of claim 8 wherein water is removed from said liquid bottoms product in a multi-effect evaporator having at least three stages.

10. The process of claim 9 wherein said multi-effect evaporator has at least four stages.

11. In a process for the recovery of acrylonitrile or methacrylonitrile from an ammoxidation reactor effluent containing acrylonitrile or methacrylonitrile, acetonitrile and heavy organic impurities in which said reactor effluent is cooled by contact with an aqueous quench liquid to produce a gaseous quench effluent containing acrylonitrile or methacrylonitrile, and acetonitrile and a liquid quench bottoms, said quench liquid being obtained by contacting said gaseous quench effluent with water, the improvement comprising removing water from said quench liquid by multiple effect evaporation prior to contacting said quench liquid with said reactor effluent.

* * * * *